US009528981B2

(12) United States Patent
Gambari et al.

(10) Patent No.: US 9,528,981 B2
(45) Date of Patent: Dec. 27, 2016

(54) DIAGNOSTIC AND THERAPEUTIC APPLICATION OF CTL AND NK FUNCTIONALLY SELECTED CELLS

(75) Inventors: Roberto Gambari, Bologna (IT); Roberto Guerrieri, Bologna (IT)

(73) Assignee: Menarini Silicon Biosystems S.p.A., Caser Maggiore (IT)

( * ) Notice: Subject to any disclaimer, the term of this patent is extended or adjusted under 35 U.S.C. 154(b) by 1236 days.

(21) Appl. No.: 12/297,041

(22) PCT Filed: Apr. 12, 2007

(86) PCT No.: PCT/IB2007/000954
§ 371 (c)(1),
(2), (4) Date: Apr. 29, 2009

(87) PCT Pub. No.: WO2007/116309
PCT Pub. Date: Oct. 18, 2007

(65) Prior Publication Data
US 2009/0325213 A1    Dec. 31, 2009

(30) Foreign Application Priority Data

Apr. 12, 2006  (IT) .............................. BO2006A0267

(51) Int. Cl.
*C12N 5/0783*   (2010.01)
*G01N 33/50*    (2006.01)

(52) U.S. Cl.
CPC ......... *G01N 33/5044* (2013.01); *G01N 33/505* (2013.01); *G01N 33/5047* (2013.01)

(58) Field of Classification Search
CPC .............. G01N 33/5044; G01N 33/505; G01N 33/5047
See application file for complete search history.

(56) References Cited

U.S. PATENT DOCUMENTS

2004/0121474 A1* 6/2004 SooHoo et al. ................ 436/63

FOREIGN PATENT DOCUMENTS

| CA | 2478815 A1 | 10/2003 | |
| WO | WO/0050589 | 8/2000 | |
| WO | WO 03/084333 | * 10/2003 | ............. A01N 63/00 |

OTHER PUBLICATIONS

Snyder et al., "Measuring the frequency of mouse and human cytotoxic T cells by the Lysispot assay: independent regulation of cytokine secretion and short-term killing", Nature Medicine, 2003, vol. 9, No. 2, pp. 231-235.*
International Search Report for PCT/IB2007/000954 dated Dec. 19, 2007.
Altomare L. et al: "Levitation and Movement of Human Tumor Cells Using a Printed Circuit Board Device Based on Software-Controlled Dielectrophoresis", Biotechnology and Bioengineering, Wiley & Sons, Hoboken, NJ, US, vol. 82, No. 4, May 20, 2003 (May 20, 2003) pp. 474-479.
Gambari R et al: "Applications to Cancer Research of Lab-on-a-Chip Devices based on Dielectrophoresis (DEP)", Technology in Cancer Research and Treatment, Adenine Press, Schenectady, NY, US, vol. 2, No. 1, Feb. 2003 (Feb. 2003), pp. 31-40.
Schoell, Wolfgang M. J. et al: "Generation of tumor-specific cytotoxic T lymphocytes by stimulation with HPV type 16 E7 peptide-pulsed dendritic cells: An approach to immunotherapy of cervical cencer", Gynecologic Oncology, vol. 74, No. 3, Sep. 1999 (Sep. 1999), pp. 448-455.
Fuchs, Alexandra B. et al: "Electronic sorting and recovery of single live cells from microlitre sized samples" Lab on a Chip, vol. 6, No. 1, 2006, pp. 121-126.
Masucci, M. G. et al: "Immune escape by Epstein-Barr virus (EBV) carrying Burkitt's lymphoma: In vitro reconstitution of sensitivity to EBV-specific cytotoxic T cells" International Immunology, vol. 4, No. 11, 1992, pp. 1283-1292.
Rickinson, A. B.: "Immune intervention against virus-associated human cancers." Annals of Oncology: Official Journal of the European Society for Medical Oncology / ESMO 1995, vol. 6 suppl 1, 1995, pp. 69-71.
International Preliminary Report and Written Opinion issued in Application No. PCT/IB2007/000954 filed Dec. 4, 2007.
Office Action in Canadian Application 2,649,244 dated Jan. 11, 2013.
Abonnenc et al., Lysis-on-Chip of single target cells following forced interaction with CTLs or NK cells on a dielectrophoresis-based array, J. Immunol., 191:3545-52 (2013).
Borgatti et al., Dielectrophoresis-based 'Lab-on-a-chip' devices for programmable binding of microspheres to target cells, Int. J. Oncol., 27(6):1559-66 (2005).
Examination Report, Canadian patent application No. 2649244, dated Dec. 13, 2013.
Examination Report, Canadian patent application No. 2880547, dated Feb. 16, 2015.
Examination Report. European Application No. 07734273.1, dated Sep. 8, 2014.
Ikeda et al., The critical role of type-1 innate and acquired immunity in tumor immunotherapy, Cancer Sci., 95(9):697-703 (2004).
Kane et al., Determination of natural killer cell function by flow cytometry, Clin. Diagn. Lab Immunol., 3(3):295-300 (1996).
Notice of Reason for Rejection (with English translation), Japanese Patent Application No. 2009-504846, dated Feb. 12, 2013.
Rosenberg, Progress in the development of immunotherapy for the treatment of patient with cancer, J Intern Med, 250(6):462-75 (2001).
Srour et al., Cytolytic activity of human natural killer cell subpopulations isolated by four-color immunofluorescence flow cytometric cell sorting, Cytometry, 11:442-6 (1990).

* cited by examiner

*Primary Examiner* — Laura Schuberg
(74) *Attorney, Agent, or Firm* — Marshall, Gerstein & Borun LLP

(57) ABSTRACT

The invention proposes a novel therapeutic and diagnostic methodology based on the use of effector cells (for example CTL and NK cells) selected for being able to induce lysis in target cells. In particular, the invention teaches how to select strains of effector cells of the immune system according to their lytic properties. It also teaches how diagnostic procedures for checking the activity of therapeutic vaccines can be improved with respect to what shown. Finally, it shows how cell therapies used at present can be improved by using this approach.

13 Claims, 6 Drawing Sheets
(2 of 6 Drawing Sheet(s) Filed in Color)

A)                    B)

DIAGNOSTIC AND THERAPEUTIC APPLICATION OF CTL AND NK FUNCTIONALLY SELECTED CELLS

FIELD OF THE INVENTION

The invention proposes a novel therapeutic and diagnostic methodology based on the use of effector cells (for example CTL and NK cells) selected for being able to induce lysis in target cells. In particular, the invention teaches how to select strains of effector cells of the immune system based on their lytic properties. It also teaches how diagnostic procedures for checking the activity of therapeutic vaccines can be improved in view of what shown. Finally, it shows how cell therapies used at present can be improved by using this approach.

It is to be noted that here and below, by the terms "effector cell/s" or, more generally, by the terms "effector/s" is understood to mean a particle (cell or generic microorganism) which has an effect on a "target" particle, in turn defined as a cell or generic microorganism on which the modification induced by the effector is expressed.

STATE OF THE ART

Some important operating properties of the immune system are determined by the action of cell groups considered as "rare". In this context, by "rare" is understood to mean a subpopulation of cells having a frequency of a part per thousand or less within a known subpopulation. It is known, for example, that the progression of diseases such as the oncologic ones can be contrasted by a subgroup of immune system cells having the property of inducing lysis in target cells having opportune characteristics. It is equally known that such effector cells are rare, so this action is not much effective if not stimulated by opportune therapeutic means.

In the therapeutic field, CTL and NK cells are now isolated through a pre-purification, combined with a clonal selection by dilution "at the limit" (10). These strategies, even though they are valid and have met applicative successes, are complex, lengthy and expensive. Furthermore, the strategy of clonal selection not always can be activated, since in many cases characteristics of receptors of target cells (for example belonging to a tumour) to be attacked are not known or only partly known.

In this regard, 1. it is known that in cases in which tumour-specific peptides are known, pre-selection of populations of tumour-specific CTLs is possible and already described in therapeutic protocols (11);
2. it is known that in most cases, neoplastic cell-specific CTLs are present in the patient in the order of $\frac{1}{1000}$-10,000 (12);
3. it is possible to isolate, with immunological techniques, populations of CTL within which tumour-specific CTLs can be identified (13);
4. single CTLs can be expanded in vitro for giving rise to homogeneous populations utilizable for following biochemical analyses (14) and, if expanded in a sufficient way, for the immunotherapy of tumours, should they maintain specific for malignant cells (15):
5. strategies completely similar to those of CTL isolation can be applied to other effector cells capable of inducing lysis in target cells;
6. the use of CTLs (and analogous effector cells) in immunotherapy is not restricted to the treatment of tumours but can concern other pathologies, among which viral pathologies (for example AIDS) and pathologies due to a bacterial infection.

Considerations carried out for CTLs are also extended for NK cells, above all as far as the use of the same is attained, if particularly active in inducing lysis in tumor cells (16).

In the light of these considerations, a method which allows to select in a reasonable time and in an efficient way highly lytic CTL clones with respect of target cells is of a great importance in a therapeutic ambit.

SUMMARY OF THE INVENTION

The present invention teaches a method for the functional selection of immune system cells by means of real-time monitoring and quantification of the lysis of target cells (for example tumor cells) mediated by T-cytotoxic lymphocytes (CTL) (1) and other cells capable of inducing lysis in opportune cell targets (typically Natural Killer cells NK) (2). Such method is based on an innovative analytical assay of CTLs activity and other lytic cells with higher capacities than those presently available. Therefore, the present invention has immediate applications in the diagnostic sector. Furthermore, such method is proposed for an effective strategy for the isolation of clones of effector cells (typically CTLs or NKs) having high activity. Therefore, the present invention has important applications in the therapeutic sector.

In particular, the invention relates to a method for the selection of immune system cells previously collected from a human being, useful in particular for the obtainment of important information to the diagnostic/prognostic check of the disease state of a neoplastic patient, including the steps of: a) let the immune system cells previously collected interact with respective target particles a modification of which, due to said interaction, is an index of a desired property of the immune system cells; b) checking the effect of the interaction on the target particles; and c) selecting, amongst immune system cells that have undergone the interaction with the target particles, those that have induced the modification in the target particles, therefore acting, towards the same, as effector cells.

Furthermore, the method according to the invention can also include the step of expanding immune system cells which have been selected at the end of step c), in order to create clones of antitumor effectors selected upstream by particular effectiveness of the lytic mechanism from heterogeneous populations (circulating or "standing" in draining lymphatic districts) of mononuclear cells.

According to a further aspect of the invention, the expansion step is performed by successive stages, carrying out between a stage and the following one a re-selection of effectors with optimal characteristics during the ex vivo amplification of possibly instable clonal populations, in particular repeating the steps a), b) and c) on at least one said possibly instable clonal population.

The invention further relates to the use of the above method for the preparation of a drug including immune system cells which have been selected through the steps a), b) and c) and/or their clones in a carrier suitable for an in vivo re-infusion with therapeutic purposes, possibly after stimulation with dendritic cells.

Finally, the invention relates to the use of a miniaturized device which allows the manipulation of effector cells and target cells without altering the biological activity thereof, in order to carry out the selection of effector cells and for the preparation of a drug of the type above indicated, as well as the use of selected and expanded lytic effector cells for the preparation of a drug for the treatment of pathologies which can be treated by in vivo re-infusion of selected and expanded lytic effector cells, characterized in that the drug only includes effector cells previously selected and/or clones of effector cells previously selected all having a substantially comparable lytic activity.

BRIEF DESCRIPTION OF FIGURES

The patent or application file contains at least one color drawing executed in color. Copies of this patent or patent application publication with color drawings will be provided by the Office upon request and payment of the necessary fee.

DETAILED DESCRIPTION

Figure 1:
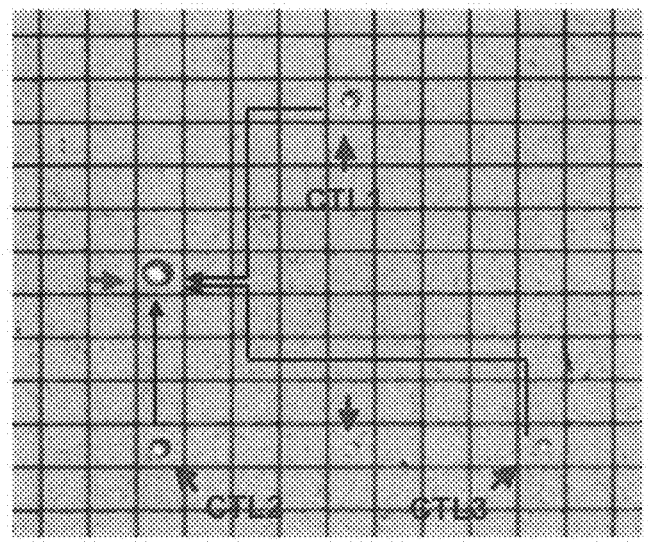
FIG. 1.A: CTLs displacement (3 CTL: red arrow) directed to hit a target tumor cell (green arrow). B: CTLs and target cell complex.
Figure 1:
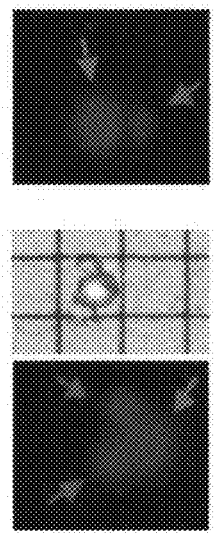

For the analysis of CTLs activity, the most currently used method is based on Cr51 release from lysated cells (3). Other methods, based on the release of non-radioactive europium (Eu3+) (4), the release of fluorescent markers (for example calcein) (5), the analysis of the esterasic activity, the use of annexin V or beta-galactosidase, have recently been adjusted. Other methods based on impedance electronic analyses are also commercialised by Acea Biosciences, which allow a real-time check of lytic effects on cell aggregates induced by immune system cells (6, 7).

These methodologies suffer from some important drawbacks. In some cases, they are based on the use of radioactive molecules (3) and always determine "average" results and not at a level of single cells (4, 5). When FACS (fluorescence-activated cell sorter) analysis (8) can be used, this requires a significant number of cells and complex and expensive instruments. In all these analyses, a real-time evaluation can not be effective.

In view of these considerations, a method allowing to monitor in a real-time and in effective way the cytolysis mediated by effector cells (for example CTLs) by extending such analysis at a level of single cell or highly lytic clones towards target cells, is certainly of a great importance in a diagnostic and therapeutic ambit.

In this regard, 1. it is known that CTL target cells can be subjected to staining using different supravital dyes, some of which can be released outside the cells if they are lysated and/or damaged (calcein (5) belongs to these supravital dyes);

2. it is known that CTL target cells can be subjected to staining using different supravital dyes which identify complex structures (mitochondria, nucleus, etc.) and which can not be released outside the cells, even if they are damaged (9);

3. opportune data processing programmes and imaging protocols can be used for the purpose of quantifying in an automated way the percentage of cells which manifest determined characteristics.

Concerning the real-time cell manipulation, the technology has recently provided some technologies. For example, tweezers lasers allow to create optical cages which can contain cells and, by moving the cages, contact cells to one another (17). It is moreover known that Lab-on-a-chip devices based on dielectrophoresis (DEP) can be very useful for displacing in a programmed way biological items (18-21). In particular, devices consisting of array-electrodes can be capable of manipulation single cells or single cell groupings.

An example of Lab-on-a-chip based on array-electrodes is shown in (21). At the base of the present invention there is the use of real-time methodologies for manipulation CTLs, NKs and target neoplastic cells and which are able to displace single cells as well, for the purpose of developing an effective method first for identification and then isolation of highly cytotoxic CTLs and therefore usable in treating neoplastic pathologies through immunoterapheutic strategies.

Experimental Procedures

Lymphoblastoid cell lines (LCL) were obtained after infection of human B lymphocytes with the Epstein-Barr Virus (EBV) strain B95.8 (26). EBV-specific peptide HPVGEADYFEY (HPV), corresponding with aa 407-417 of EBNA1) protein was used for stimulation. Lymphocytes from peripheral blood (PBL) from a HLA-B35 donor were plated at a concentration of 3.5×106 cells per well in 24-well plates in a culture medium RPMI 1640, 10% FCS (Hyclone) and stimulated with HPV peptide (10 μM). Cultures were again stimulated after 7 and 14 days and the medium was supplemented with 10 U/ml rIL-2 (Chiron). At days 14 and 21 cultures of T-cells were analyzed by CTL activity using appropriate cytotoxicity assays (51Cr-release) (3).

Remarks on Obtained Results

Results of such study are shown in the examples reported in FIGS. 1-6. Examples are given for illustrative purpose and are not intended to limit the scope of the invention in any way. In FIG. 1 the displacement of three CTLs (red arrows) directed to hit a single target tumor cell, by generating complexes shown in the right side of the figure, is reported, wherein CTLs appear in red and the target cell in green.

Figure 2:
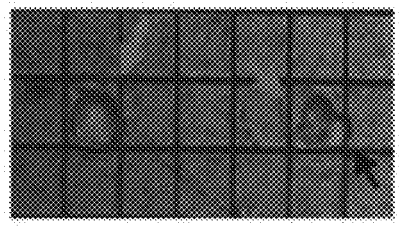
FIG. 2. Interaction of CTLs (black arrows) and of one target cell (green arrow): the target cell is in an advanced lysis state.
Figure 2:
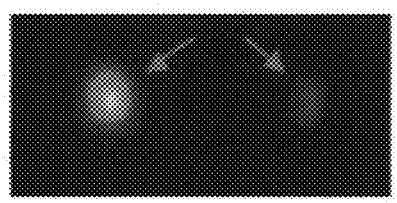
Figure 2:
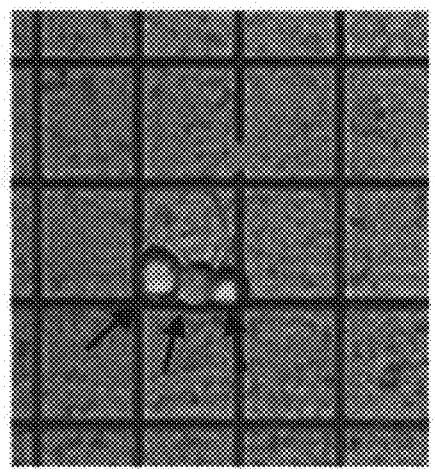
Figure 3:
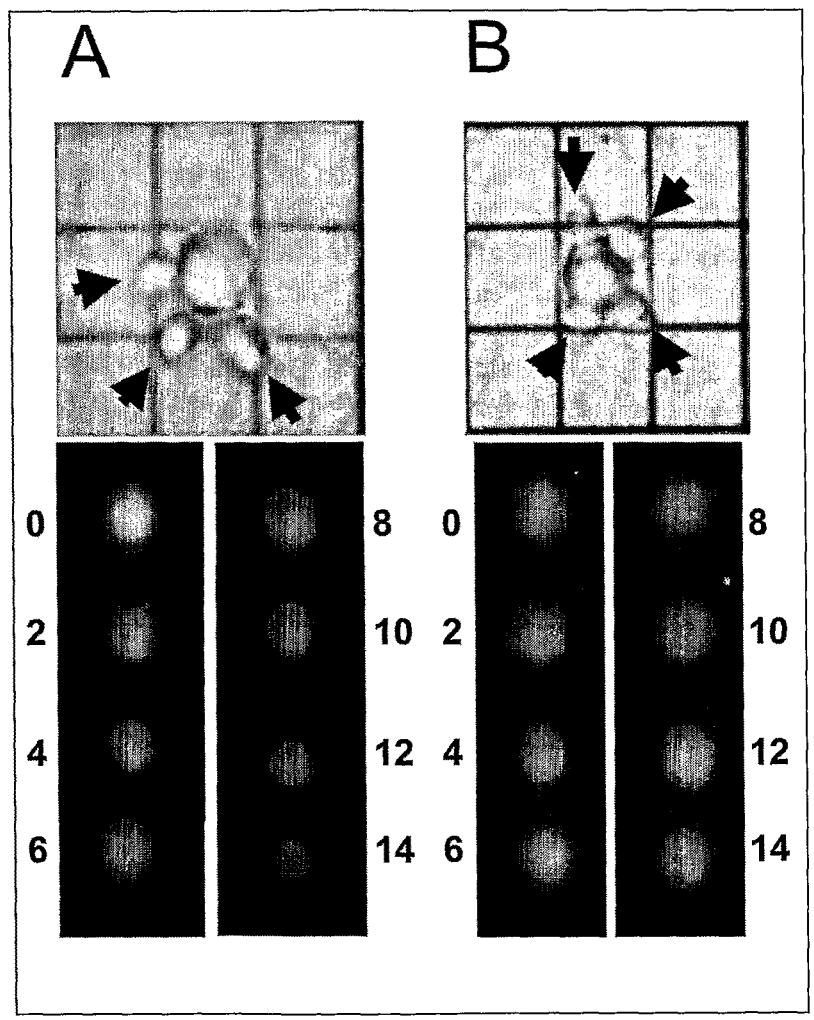
FIG. 3.A: lysis kinetics of target cells. B: non pre-activated CTLs.
Figure 4:
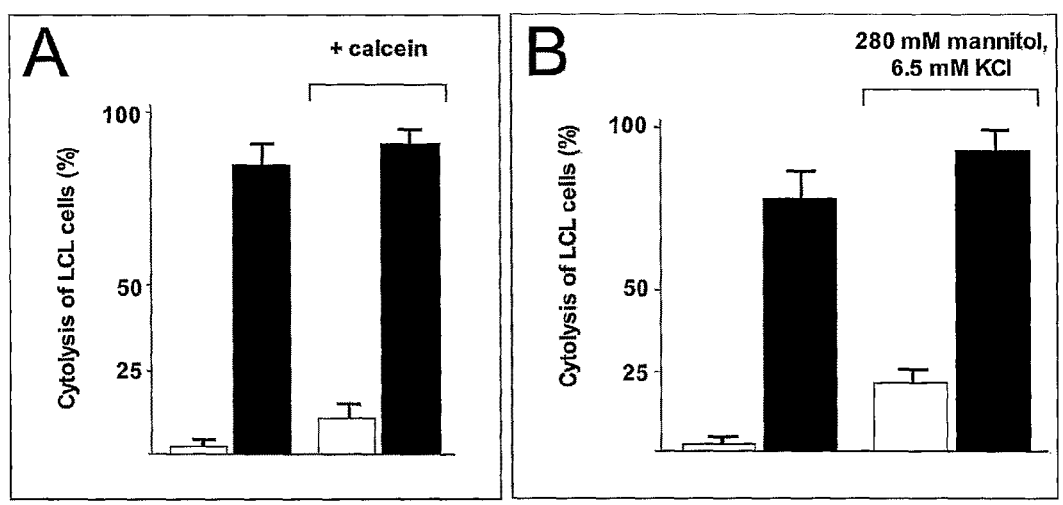
FIG. 4. A: calcein effect on lytic activity of CTLs measured through lysis % in a Cr51 release assay. In black bar graphs the specific lysis of target LCLs is reported (B35, loaded with EBV peptide), in the presence (on the left) or in the absence (on the right) of calcein; in white bar graphs, the control represented by LCLs unloaded with the peptide is reported. B. effect of the mannitol buffer on the lytic activity of CTLs (Cr51 release assay). In black bar graphs, the specific lysis of target LCLs is reported, in a mannitol-containing buffer (on the left) or in a standard buffer (RPMI; on the right); in white bar graphs, the control represented by LCLs unloaded with peptide is shown.

We have surprisingly found that CTLs, displaced on a Lab-on-a-chip containing array electrodes can be contacted with neoplastic target cells and are capable to lysate them in a very quick time (varying from 8 to 20 minutes). If cells are marked with calcein, they are fluorescent if intact, loosing the fluorescence if damaged by CTLs (FIG. 2 and FIG. 3). By carrying out double stainings using dyes for mitochondria or DNA, cells damaged by CTLs lose their fluorescence of calcein maintaining the one of specific dyes for mitochondria or DNA. Therefore, through a fluorescence microscope analysis (possibly using imaging programmes), it is possible to discriminate active CTLs from inactive CTLs. Non-selected CTLs do not show lytic activity on LCLs non pre-loaded with peptide.

From the other hand, as it has recently been described (22-25), cells manipulated by DEP maintain their phenotype and their differentiated features. According to the present invention, it has been noted that also the cytolytic activity and the detection of an optical signal (fluorescence) are not altered by this type of manipulation. This approach, therefore, is suitable for the immediate identification and following isolation and expansion of active CTL clones, as well as other cell populations which show a cytolytic activity towards determined cell targets.

In addition to optical imaging techniques used in this demonstration, it is known that impedance measurement techniques (6) allow to check the state of single cells with a high level of accuracy. The optical technique presented in this embodiment is therefore to be intended as merely exemplificative of a more general method.

FIG. 2 shows details of cells in an advanced lysis state after interaction with CTLs. In particular, in the right part of figure a lysated target cell by three CTLs (black arrows) can be observed (green arrow). FIG. 3 (panel A) shows lysis kinetics in CTLs/target cells aggregates. In B it is pointed out that non-preselected CTLs are not lytic. As it can be seen, the strategy allows to analyze lysis kinetics after a contact with CTLs and to identify CTL patterns with a high cytolytic activity.

FIG. 4A shows that a marking with calcein does not alter the lysis mechanism or the specific recognition of (LCL) HLA-B35 lymphocytes loaded with EBV peptide from CTLs. In FIG. 4B there is also shown that neither dielectrophoresis nor mannitol-containing buffer have any effects on this mechanism, a result which is aligned with what has been checked by others for the gene expression profile (37) and the growth ability of K562 (35, 36), which do not result to be altered by dielectrophoresis.

Figure 5:
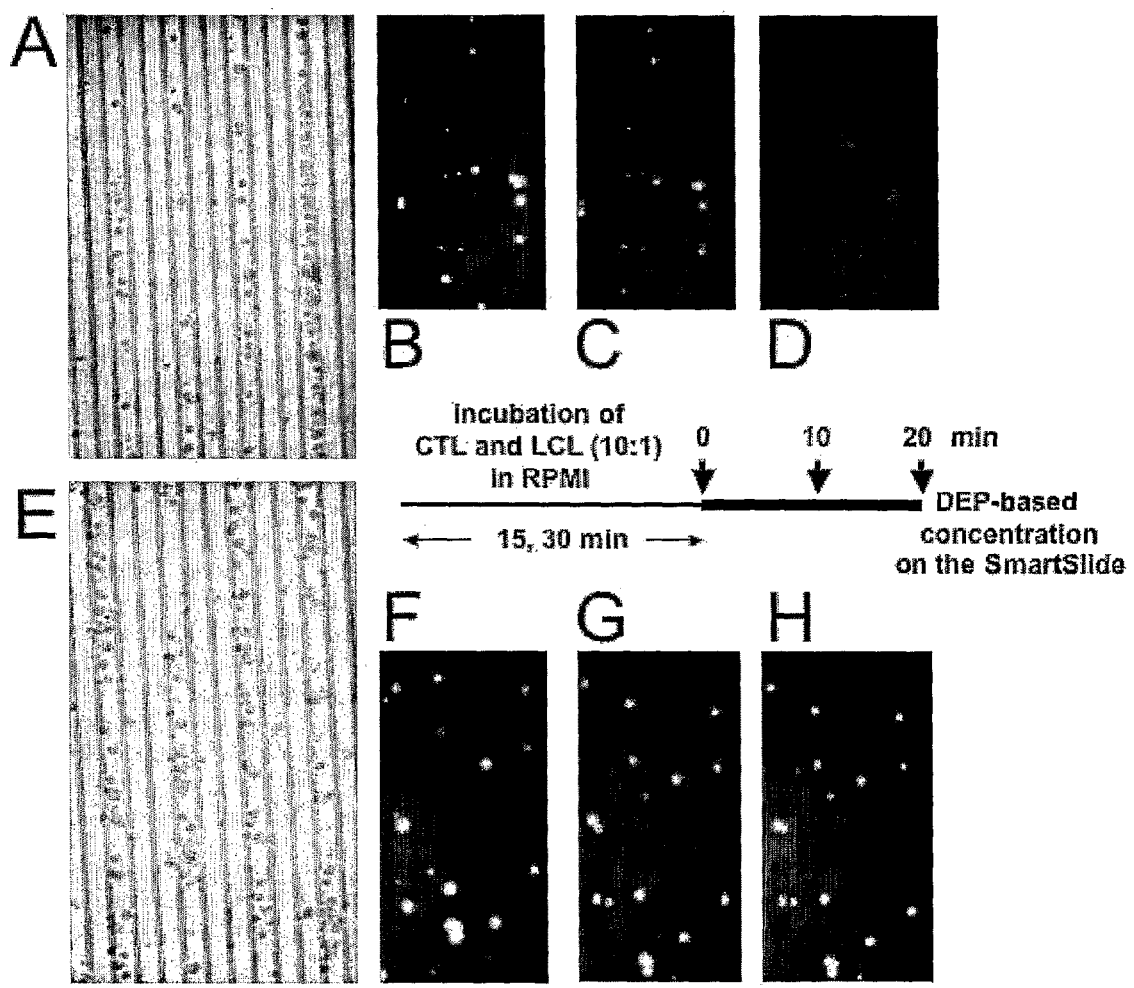
FIG. 5. Detection of specific lysis of target LCLs loaded with the EBV peptide in a mannitol buffer, after DEP displacement and loading with calcein, on SmartSlide®. A-D panels: lysis of HPV-positive LCLs by HPV-specific CTLs has been detected after 10' and 20'; panels E-H: on the contrary, EBV-specific CTLs do not lysate LCLs unloaded with the peptide.
Figure 6:
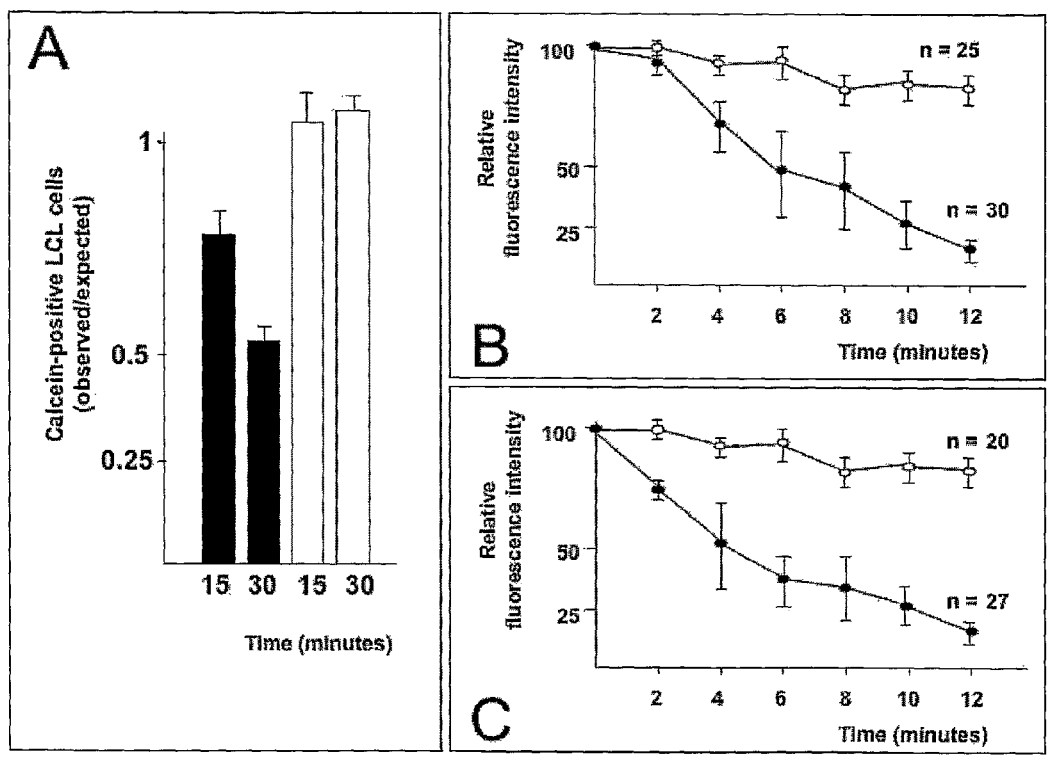
FIG. 6. Reported data are the mean of three experiments wherein the decrease of the fluorescence signal (calcein) is detected over time, due to lysis of LCL-B35 loaded with EBV peptide, by specific CTLs after co-incubation in a standard buffer (RPMI) for 15' (panel B) or 30' (panel C). A parallel control detection (white bar graphs in A; empty symbols in C) shows that lysis is specific; in fact, it is absent if LCLs are not loaded with the EBV peptide; the decrease of the signal intensity over time is, in this case, minimum.

The maintenance of the specificity of recognition reactions and lysis in the used experimental conditions (mannitol buffer and displacement through dielectrophoresis) has further been checked in experiments shown in FIGS. 5 and 6. In FIG. 6 there is also shown kinetics of fluorescence intensity variation following to specific lysis of LCLs from CTLs, which can already be pointed out within the first 8-10 minutes from DEP treatment, also starting from a limited number of cells (no.=25, 30, 20, 27). In conclusion, it has surprisingly been found that the specificity of the immune reaction remains preserved in this experimental context. In fact, it is absolutely not obvious that the immune reaction gives rise to a selective behaviour also in the presence of an extremely reduced number of cells. In particular, the environment in which this kind of manipulation takes place prevents aggregation phenomena amongst cells which, on the contrary, occur in all other methodologies. Despite this, the finding of the selectivity and specificity of the immune reaction opens up doors to an important series of teachings of this patent.

The fact that cytotoxic effectors (CTLs in the reported example, but also NK cells and other) can be enumerated ex vivo in a real-time and that this analysis is not based on "surrogate endopoints" (e.g. the expression of a surface specific marker of the effector, the release of a lymphokine, the expression of differentiation antigens, etc.) but rather on the online and real-time quantitative reading of the lytic effectiveness at a level of a single cell, is innovative and with a great importance. It is known, in fact, that not all T-lymphocytes which recognize a given antigen are equally lytic (2, 28) and that the percentage of mature phenotype-lymphocytes increases during vaccinations (29). It is expected that the use of the direct cytotoxicity as an endpoint greatly correlates with the clinical prognosis with respect to the use of surrogate endopoints, and allows a more accurate monitoring of the effectiveness of the vaccine preparations in inducing a specific immunity. Furthermore, the presence of anti-tumour T-lymphocytes is often observed in concomitance with a relapse and return of a disease also in patients not recently vaccinated (30).

Being the technique of cell recovery after the manipulation (33) a known art, this procedure has therapeutic involvements. The isolation and the recovery of effector cells with a high lytic activity allows the "in vitro" cultivation of highly selected cells, with the aim of carrying out biochemical studies and expanding the selected populations. Both strategies have deep implications in immunotherapy of tumours.

In fact, the isolation of high selectivity cytotoxic effectors from heterogeneous populations (circulating or "standing" in draining lymphatic districts) of mononuclear cells allows (a) the clonal expansion of antitumor effectors selected upstream, for the particular effectiveness of the lytic mechanism; (b) the re-selection of effectors during the ex vivo amplification of possibly instable clonal populations. Technologies for in vivo re-infusion for therapeutic purposes, possibly after stimulation with dendritic cells, are available (31). The effectiveness of local and/or systemic re-infusion of these effectors, and the take of the autologous infusion can also be monitored over time and correlated with the immune state and the course of the disease (31).

The possibility of expanding in vitro highly lytic cells, changing, if necessary, the phenotype and re-infusing them in patients suffering from neoplasia (adoptive-cell-transfer therapy) has been a subject of multiple studies (28-30, 32). In this experimental strategy, the rapid identification of effector cells with a high lytic activity and the ability of generating cell loadings having a therapeutic importance however maintaining the gene stability is still a limiting factor.

The strategy subject of this patent is compatible with a lowering of times and an improvement of the selection procedure of cells with high lytic activity, facilitating, from one side, the identification of target tumor antigens, from the other side the expansion of cells usable in immunotherapy. If, by way of example, the method suggested in (32) is considered for obtaining a functional selection of useful strains of cells potentially having an induction activity of lysis in target cells, the improvement in the selection quality obtained by the present methodology is better appreciated. The technique in (32) starts from the observation that there are cell strains, TILs or Tumor Infiltrating Lymphocytes, capable of infiltrating in the tumor tissue and exerting a lytic activity towards carcinogenic cells. Also in this case, the number of TILs found in patients is lower than the required for obtaining a disease remission. The protocol can then be summarized in the following steps: 1) obtaining of biopsy from the patient, 2) treatment of the tissue so as to allow the in vitro infusion of opportune nutritive and growth factors for the desired cells, 3) after the growth step has ended, purification of cell strains of TILs and removal of tumor cells, 4) re-infusion in patients of the cells thus obtained. It is known that only a fraction of TILs obtained in this way shows lytic activities and therefore, as the quantity of cells re-infused in the patient for limiting undesired side effects can not be exceeded, the therapy has a restricted effectiveness. The methodology proposed in this patent reduces in a significant way the limitations of the one discussed herein as 1) the selection of effector cells can be extended at cell lines also existing in the peripheral blood and is not limited to TILs; 2) the functional selection produces a set of strains whose lytic ability is known; 3) it allows to improve the expansion procedure of these cell lines owing to the possibility of monitoring in different expansion steps the stability of the concerned cell lines; 4) it reduces the cell loading required for the therapy and therefore, on the same material re-infused in the patient, provides a more aimed action. The point 3) improves in a significant way the state of the art relating to the expansion of CTL-type cell lines which are know to change the lytic phenotype after a certain number of expansions. In the extreme case in which the availability of a single cell having the desired lytic features is downstream the selection procedures and it is necessary to reach cell loadings having therapeutic valences of the order of some millions of cells, about 25 or 30 expansion cycles are required.

This number of cycles is such not to maintain the genic stability of the involved cells, so that subpopulations having a different lytic phenotype are generated. The presented invention teaches how to solve this problem. In fact, the functional selection of cells can be repeated at different stages of the growth procedure and for example when, after 10 or 12 growth cycles, some thousand of cells are available. The purification of the cell line can be restored trough an extended application of the functional selection above disclosed. It is in fact possible to maintain target cell lines obtained by the biopsy and repeat the suggested method for eliminating lytic cells having an undesired phenotype. The elimination of lytic cells at this expansion level is consistent with selection technologies based on electronic techniques and therefore pure lines are again obtained. A further expansion for a number of cycles equal to 10 or 12 produces a number of lytic cells having adequate numbers for therapeutic applications. Even if at this point the cell number is such to prevent an examination at a single cell level of the stability of the lytic phenotype, the number of growth cycles without control of the phenotype is now very reduced and therefore cells can be considered as proper reproductions of the original ones.

The invention further contemplates the use of any device suitable for cell manipulations which do not alter the biological activity of effector cells (in this case CTLs).

From the other hand, the invention relates to the isolation of each type of cell (including NK cells) capable of lysating target cells.

Finally, the invention is applied to all pathologies for which the cytolytic activity of effector cells (NKs or CTLs) can then be mainly directed, as above observed, to neoplastic pathologies, infective pathologies, autoimmune pathologies and inflammatory pathologies of acute and chronic type.

It is finally provided, hereinafter, a bibliographic list of public documents on which we have referred to so far, showing them with their reference number, whose content is to be intended incorporated for the required parts in this description by reference.

REFERENCES

1. Bollard C M, Savoldo B, Rooney C M, Heslop H E. Adoptive T-cell therapy for EBV-associated post-transplant lymphoproliferative disease. Acta Haematol. 2003; 110(2-3):139-48.

2. Mariani E, Monaco M C, Sgobbi S, de Zwart J F, Mariani A R, Facchini A. Standardization of a micro-cytotoxicity assay for human natural killer cell lytic activity. J Immunol Methods. 1994; 172(2):173-8.

3. Hillman G G, Roessler N, Fulbright R S, Pontes J E, Haas G P. 51Cr-release assay adapted to a 96-well format sample reading. Biotechniques. 1993; 15(4):744-9.

4. Nagao F, Yabe T, Xu M, Yokoyama K, Saito K, Okumura K. Application of non-radioactive europium ($Eu^{3+}$) release assay to a measurement of human natural killer activity of healthy and patient populations. Immunol Invest. 1996; 25(5-6):507-18.

5. Neri S, Mariani E, Meneghetti A, Cattini L, Facchini A. Calcein-acetyoxymethyl cytotoxicity assay: standardization of a method allowing additional analyses on recovered effector cells and supernatants. Clin Diagn Lab Immunol. 2001; 8(6):1131-5.

6. Yu N, Atienza J M, Bernard J, Blanc S, Zhu J, Wang X, Xu X, Abassi Y A. Real-time Monitoring of Morphological Changes in Living Cells by Electronic Cell Sensor Arrays: An Approach to Study G Protein-coupled Receptors. Analytical Chemistry, 2006; 78(1), 35-43.

7. L. L. Sohn, O. A. saleh, G. R. facer, A. J. Beavis, R. S. Allan, D. A. Notterman. Capacitance cytometry: measuring biological cells one by one. Proc Natl Acad Sci USA. 2000; 97, 10687-10690

8. Goldberg J E, Sherwood S W, Clayberger C. A novel method for measuring CTL and NK cell-mediated cytotoxicity using annexin V and two-color flow cytometry. J Immunol Methods. 1999; 224(1-2): 1-9.

9. Bachy M, Bonnin-Rivalland A, Tilliet V, Trannoy E. Beta galactosidase release as an alternative to chromium release in cytotoxic T-cell assays. J Immunol Methods. 1999; 230(1-2):37-46

10. Micheletti F, Canella A, Vertuani S, Marastoni M, Tosi L, Volinia S, Traniello S, Gavioli R. Supra-agonist peptides enhance the reactivation of memory CTL responses. J. Immunol. 2000; 165(8):4264-71.

11. Palmowski M, Salio M, Dunbar R P, Cerundolo V. The use of HLA class I tetramers to design a vaccination strategy for melanoma patients. Immunol Rev. 2002; 188:155-63.

12. Bouma G J, van der Meer-Prins P M, van Bree F P, van Rood J J, Claas F H. Determination of cytotoxic T-lymphocyte precursor frequencies using europium labeling as a nonradioactive alternative to labeling with chromium-51. Hum Immunol. 1992; 35(2):85-92.

13. Ikeda H, Chamoto K, Tsuji T, Suzuki Y, Wakita D, Takeshima T, Nishimura T. The critical role of type-1 innate and acquired immunity in tumor immunotherapy. Cancer Sci. 2004; 95(9):697-703.

14. Mukherjee P, Tinder T L, Basu G D, Pathangey L B, Chen L, Gendler S J. Therapeutic efficacy of MUC1-specific cytotoxic T lymphocytes and CD137 co-stimulation in a spontaneous breast cancer model. Breast Dis. 2004; 20:53-63.

15. Rosenberg S A. Progress in the development of immunotherapy for the treatment of patients with cancer. J Intern Med. 2001; 250(6):462-75.

16. Hallett W H, Murphy W J. Natural killer cells: biology and clinical use in cancer therapy. Cell Mol Immunol. 2004; 1(1):12-21.

17. Wang Y, Botvinick E L, Zhao Y, Berns M W, Usami S, Tsien R Y, Chien S. Visualizing the mechanical activation of Src. Nature. 2005; 434:1040-5.

18. Voldman J, Braff R A, Toner M, Gray M L and Schmidt M A. Holding forces of single-particle dielectrophoretic traps. Biophys J. 2001; 80, 531-541.

19. Gascoyne P R and Vykoukal J. Particle separation by dielectrophoresis. Electrophoresis. 2002; 23, 1973-83.

20. Fiedler S, Shirley S G, Schnelle T and Fuhr G. Dielectrophoretic sorting of particles and cells in a microsystem. Anal Chem. 1998; 70, 1909-1915.

21. Manaresi, N., Romani, A., Medoro, G., Altomare, L., Leonardi, A., Tartagni, M. and Guerrieri, R. (2003) A CMOS Chip for individual cell manipulation and detection. IEEE J. Solid-State Circuits 38, 2297-2304.

22. Altomare L, Borgatti M, Medoro G, Manaresi N, Tartagni M, Guerrieri R and Gambari R. Levitation and Movement of Human Tumor Cells using a Printed Circuit Board Device Based on Software-controlled Dielectrophoresis. Biotechnol Bioeng. 2003; 82, 474-479.

23. Gambari R, Borgatti M, Altomare L, Manaresi N, Medoro G, Romani A, Tartagni M. and Guerrieri R. Applications to cancer research of "lab-on-a-chip" devices based on dielectrophoresis (DEP). Technol Cancer Res Treat. 2003; 2, 31-40.

24. Borgatti M, Altomare L, Baruffa M, Fabbri E, Breveglieri E, Feriotto G, Manaresi N, Medoro G, Romani A, Tartagni M, Gambari R and Guerrieri R. Separation of white blood cells from erythrocytes on a dielectrophoretis (DEP) based 'Lab-on-a-chip' device. Int J Mol Med. 2003; 15, 913-920.

25. Huang Y, Joo S, Duhon M, Heller M, Wallace B and Xu X. Dielectrophoretic cell separation and gene expression profiling on microelectronic chip arrays. Anal Chem. 2002; 74, 3362-3371.

26. Salter, R. D., and P. Cresswell. 1986. Impaired assembly and transport of HLA-A and -B antigens in a mutant TxB cell hybrid. EMBO J. 5:943-949)

27. Kuroki M, Hachimine K, Huang J, Shibaguchi H, Kinugasa T, Maekawa S, Kuroki M. Re-targeting of cytotoxic T lymphocytes and/or natural killer cells to CEA-expressing tumor cells with anti-CEA antibody activity. Anticancer Res. 2005; 25(6A):3725-32.

28. Wang R F, Rosenberg S A. Human tumor antigens for cancer vaccine development. Immunol Rev. 1999; 170:85-100.

29. Rosenberg S A. Shedding light on immunotherapy for cancer. N Engl J. Med. 2004; 350(14):1461-3.

30. Rosenberg S A. Progress in human tumour immunology and immunotherapy. Nature. 2001; 411(6835):380-4.

31. Zitvogel L, Terme M, Borg C, Trinchieri G. Dendritic cell-NK cell cross-talk: regulation and physiopathology. Curr Top Microbiol Immunol. 2006; 298:157-74.

32. Dudley M E, Rosenberg S A. Adoptive-cell-transfer therapy for the treatment of patients with cancer. Nat Rev Cancer. 2003; 3(9):666-75.

33. Alexandra B. Fuchs, Aldo Romani, Delphine Freida, Gianni Medoro, Melanie Abonnenc, Luigi Altomare, Isabelle Chartier, Dorra Guergour, Christian Villiers, Patrice N. Marche, Marco Tartagni, Roberto Guerrieri, Francois Chatelain and Nicolo Manaresi. Electronic sorting and recovery of single live cells from microlitre sized samples. Lab Chip, 2006; 6:121-126

The invention claimed is:

1. Method for the isolation of immune system cells having cytolytic activity from a population of immune system cells previously collected from a human being, comprising the steps of: a) interacting the population of immune system cells with target cells by inducing the contact of a single cell from the population of immune system cells with a target cell, wherein the immune system cells having cytolytic activity are capable of inducing lysis in the target cells; b) identifying which target cells have undergone lysis; and c) selecting immune system cells having cytolytic activity by displacing on a single cell basis only those immune system cells that have induced said lysis of the target cells within 20 minutes of interacting the population of immune system cells with target cells; wherein said steps a), b), and c) are carried out by displacing single cells using a miniaturized device based on a dielectrophoresis-based array which allows real-time monitoring and manipulation of single immune system cells having cytolytic activity without altering the cytolytic activity of the immune system cells having cytolytic activity.

2. Method according to claim 1, wherein the target cells are selected from the group consisting of: lymphoblastoid cells, tumor cells, and microorganisms.

3. Method according to claim 1, wherein said immune system cells having cytolytic activity are T-cytotoxic lymphocytes (CTL) and/or Natural Killer (NK) cells.

4. Method according to claim 1, wherein selecting only those immune system cells having the cytolytic activity that have induced lysis of the target cells is carried out either by optical imaging techniques preceded by marking at least said target cell, or by impedance measurement techniques.

5. Method according to claim 1, further comprising the step of collecting and expanding the selected immune system cells having cytolytic activity in order to create clones of the immune system cells having cytolytic activity.

6. Method according to claim 5, wherein said expansion step is carried out by repeating said steps a), b) and c) on the immune system cells having cytolytic activity which have been selected at the end of the step c).

7. A method according to claim 1, wherein the miniaturized device comprises a lab-on-a-chip device.

8. The method according to claim 1, wherein said human being is a neoplastic patient.

9. The method according to claim 1, wherein the target cells are loaded with a fluorescent marker.

10. The method according to claim 9, wherein step b) comprises detecting a decrease of the fluorescence signal from the target cells following lysis of the target cells by the immune system cells having cytolytic activity.

11. The method according to claim 9, wherein the fluorescent marker is calcein.

12. The method of claim 1, wherein identifying which target cells have undergone lysis is performed within 10 minutes of interacting the population of immune system cells with target cells.

13. The method of claim 1, wherein at least one target cell is loaded with an antigen, and wherein the immune system cells having cytolytic activity specifically induce lysis only in target cells loaded with said antigen.

* * * * *

UNITED STATES PATENT AND TRADEMARK OFFICE
CERTIFICATE OF CORRECTION

PATENT NO. : 9,528,981 B2  
APPLICATION NO. : 12/297041  
DATED : December 27, 2016  
INVENTOR(S) : Roberto Gambari et al.

Page 1 of 1

It is certified that error appears in the above-identified patent and that said Letters Patent is hereby corrected as shown below:

On the Title Page

At item (73), Line 2, "Caser" should be -- Castel --.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*